US005529751A

United States Patent [19]
Gargas

[11] Patent Number: 5,529,751
[45] Date of Patent: Jun. 25, 1996

[54] AQUARIUM PH ADJUSTMENT APPARATUS

[75] Inventor: Joseph E. Gargas, South Holland, Ill.

[73] Assignee: The Wardley Corporation, Seacaucus, N.J.

[21] Appl. No.: 250,722

[22] Filed: May 27, 1994

[51] Int. Cl.$^6$ .............................. G01N 31/22; C02F 1/66
[52] U.S. Cl. ........................... 422/61; 210/85; 210/96.1; 210/169; 210/198.1; 206/569; 283/115; 422/55; 436/163
[58] Field of Search ........................... 210/85, 96.1, 169, 210/198.1, 743, 749; 422/61, 55; 206/569; 283/115; 436/163, 164, 166

[56] References Cited

U.S. PATENT DOCUMENTS

| | | | |
|---|---|---|---|
| 4,016,079 | 4/1977 | Severin | 210/169 |
| 4,195,059 | 3/1980 | Whitcher et al. | 422/61 |
| 4,409,182 | 10/1983 | Macklem | 422/61 |
| 4,663,126 | 5/1987 | Gould et al. | 422/61 |
| 4,904,605 | 2/1990 | O'Brien et al. | 422/61 |
| 4,940,551 | 7/1990 | Riggs et al. | 210/96.1 |
| 5,326,482 | 7/1994 | Lessard et al. | 210/743 |
| 5,342,543 | 8/1994 | Morris et al. | 252/190 |

*Primary Examiner*—Peter A. Hruskoci
*Assistant Examiner*—Theodore M. Green
*Attorney, Agent, or Firm*—Stroock & Stroock & Lavan

[57] ABSTRACT

An apparatus is provided for adjusting the pH of water in an aquarium. A measured sample of the aquarium's water is combined with a chemical indicator. The pH of the aquarium is then determined. If the pH is too low, drops of basic fluid having a known pH are added to the sample until the desired pH has been achieved. The number of drops of base added is then converted to an amount of a secondary base, based on the volume of water in the aquarium. This quantity of secondary base is then added to the aquarium and the pH is thereby adjusted to the desired level. Similarly, if the pH of the aquarium needs to be lowered, drops of acid are added to the sample and the number of drops of acid required to bring the sample to the correct pH is converted to a quantity of a secondary acid to be added to the aquarium to the lower the pH to the desired level.

15 Claims, 2 Drawing Sheets

AQUARIUM PH ADJUSTMENT APPARATUS

BACKGROUND OF THE INVENTION

This invention relates generally to aquariums for keeping pet fish and more particularly to an apparatus and method for adjusting the pH of an aquarium to a desired level. Maintaining tropical fish in an aquarium is an extremely popular hobby. However, many fish are sensitive to small variations in pH and become unhealthy or die if the pH of the aquarium reaches an unacceptable value. Therefore, the pH of an aquarium must be maintained at an acceptable value.

Various factors affect the pH of aquarium water. Municipal water is treated with various chemicals, contains various salts and will vary from region to region. Furthermore, well water will also vary in pH from location to location. Moreover, the wastes produced by aquatic plants and fish in the aquarium also affect the pH. Therefore, even if the pH of an aquarium is adjusted to a desired level, it can change with time or with the addition of replacement water.

Accordingly, it is desirable to provide hobbyists with a kit so that they can conveniently adjust the pH of their fish tanks. pH test kits that are conventionally used by aquarium hobbyists suffer from several drawbacks. When using these kits, the pH of the water is determined and then acid or base is added in an unquantified fashion, followed by re-testing, until the desired pH is achieved. Conventional pH test kits for aquarium hobbyists lack a quantification system so that the acid or base can be added to adjust the pH in one step in a precise and a quantified manner.

One reason why such a kit has not been popularized is due to the conventional belief that the pH of an aquarium should be adjusted gradually in several steps in order to avoid pH shock. It is conventionally believed that pH shock will injure aquarium fish if the pH of the water is adjusted too quickly. Thus, conventional methods and apparatuses for adjusting the pH do so in a slow gradual manner, rather than in a more convenient manner.

Accordingly, it is desirable to provide an apparatus and method for adjusting the pH for an aquarium in a quick precise manner.

SUMMARY OF THE INVENTION

Generally speaking, in accordance with the invention, a method and apparatus are provided for adjusting the pH of an aquarium. A measured sample of the aquarium's water is combined with a chemical indicator. The pH of the aquarium is then determined by comparing the color of the sample to a pH color chart for the indicator. If the pH is too low, drops of basic fluid having a known pH are added to the sample until the color achieves the desired hue indicating that the desired pH has been achieved. The number of drops of base added is then converted to an amount of a secondary base, based on the volume of water in the aquarium. This quantity of secondary base is then added to the aquarium and the pH is thereby adjusted to the desired level. Similarly, if the pH of the aquarium needs to be lowered, drops of acid are added to the sample and the number of drops of acid required to bring the sample to the correct color is converted to a quantity of a secondary acid to be added to the aquarium to the lower the pH to the desired level.

Accordingly, it is an object of the invention to provide an improved method and apparatus for adjusting the pH of an aquarium.

Another object of the invention is to provide a method and apparatus for adjusting the pH of an aquarium with the single addition of an acid or base.

A further object of the invention is to provide a method and apparatus for adjusting the pH of an aquarium in a quantifiable manner.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

The pH of water in an aquarium is adjusted, in accordance with a preferred embodiment of the invention, in the following manner. A test sample of a selected volume of water is removed from the aquarium. A selected number of drops of a known chemical indicator are then added to the sample. The color of the sample is then compared to a pH color chart for that particular chemical indicator and the initial pH of the aquarium is noted. It is then determined whether the pH of the aquarium water must be raised or lowered to a target pH, based on the particular needs of the fish in the aquarium.

If the pH must be lowered, a primary acid of a known concentration is added drop-wise to the sample until the color of the sample indicates that the target pH has been reached. The number of drops of acid added to the sample is then converted to an amount of a secondary acid to be added to the aquarium. The secondary acid is then added to the aquarium and will adjust the pH of the aquarium to the desired value. If the addition of the indicator to the test sample shows that the pH of the aquarium must be raised, a similar process is conducted with bases to raise the pH to the desired target level.

A pH adjustment kit prepared in accordance with a preferred embodiment of the invention includes a conversion chart for converting the amount of primary acid or primary base added to the test sample to an amount of secondary acid or secondary base to be added to the aquarium. Such a conversion chart can include an acid demand section for determining the amount of acid to add to an aquarium to lower the pH to a target level and a base demand section for determining how much base to add to an aquarium to raise the pH to a desired level.

Each of the acid demand sections and base demand sections of the conversion chart can include a column listing common capacities of aquariums, such as 10, 15, 20, 30 and 55 gallons. Values for differently sized aquariums can be calculated, based on these values.

The conversion chart can also include a row corresponding to drops of primary acid or primary base added to the test sample to change the test sample to the desired pH. Then, by finding the intersection of the column and row associated with both the aquarium capacity and the number of drops added to the test sample, the amount of secondary acid or secondary base to be added can be merely read off the conversion chart and added to the aquarium.

Figure 1:
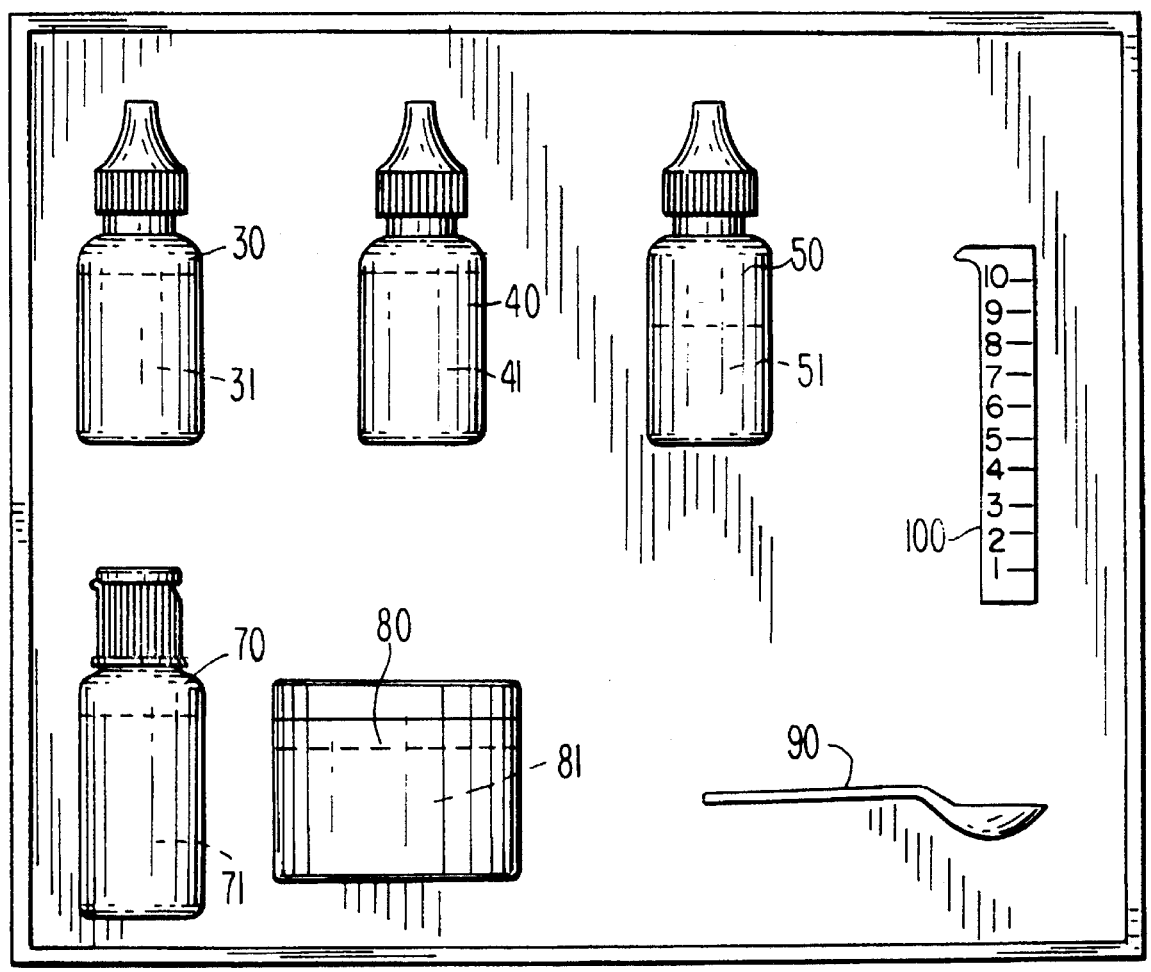
FIG. 1 is a perspective view of a kit for adjusting the pH of an aquarium in accordance with an embodiment of the invention, including a vile for receiving a sample of aquarium water and for measuring fluids to be added to the aquarium, a bottle containing an indicator to be added to the sample in the cylinder, a bottle containing acid for lowering the pH of the sample, a bottle containing a base for raising the pH of the sample, a container for storing acid to be added to the aquarium in order to lower the pH thereof, a container for a base to be added to an aquarium to raise the pH thereof and a spoon of measured size for dispensing powder base to an aquarium for raising the pH thereof.
Figures 2, 3:
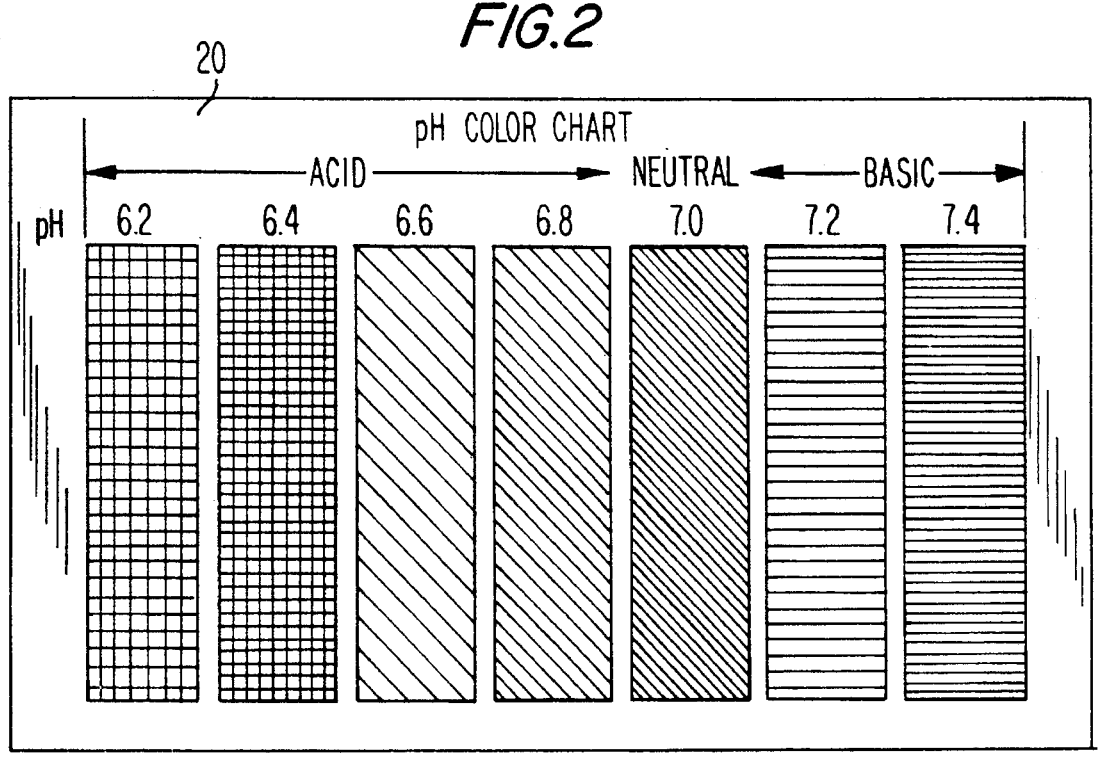
FIG. 2 is a pH color comparison chart for determining the number of drops of a primary acid or base to be added to the sample in the cylinder of FIG. 1.
FIG. 3 is a conversion chart used to convert drops of primary acid or base into a quantity of a secondary acid or base needed to adjust the pH of the aquarium to the desired level, in accordance with the invention.

A pH adjustment kit for an aquarium, constructed in accordance with a preferred embodiment of the invention, is shown generally as kit 200 in FIG. 1, and also includes a pH color comparison chart 20 shown in FIG. 2 and a conversion chart 60 shown in FIG. 3.

Figure 4:
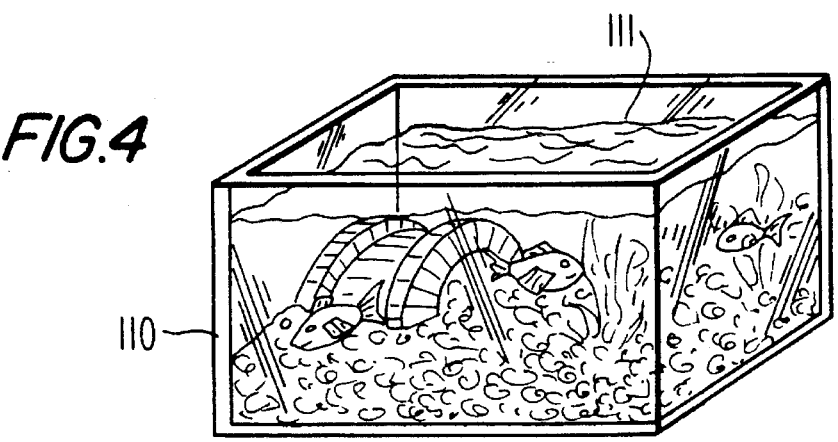
FIG. 4 is a perspective view of an aquarium.

Kit 200 also includes a graduated cylinder 100, in the form of a marked vile having a rectangular cross section, which is shown having a capacity of 10 ml. In a preferred embodiment of the invention, a 5 ml test sample of aquarium water 111 from an aquarium 110, shown in FIG. 4, is placed into graduated cylinder (vile) 100. Thus, to aid the hobbyist, cylinder 100 should be formed with the 5 ml level clearly marked so that it is convenient to obtain a precise 5 ml sample. Cylinder 100 should also be graduated to assist in other measurements needed in order to assist in the pH adjustment method.

Kit 200 also includes an indicator bottle 30 containing an indicator 31 for adding to the test sample of water 111 in cylinder 100. After indicator 31 is added, the color of the test sample in cylinder 100 is compared to color chart 20 of FIG. 2 to determine the pH of water 111 in aquarium 110. Indicator 31 is preferably bromothymol blue.

Bromothymol blue was found to exhibit easily recognizable color variations in a pH range of about 6.2 to about 7.4 when two drops are added to a 5 ml sample. pH color chart 20 should be prepared with specially selected dyes so that an accurate color comparison can be made. The colors of chart 20 should be calibrated to accurately reflect the color of a 5 ml sample of water, to which two drops of bromothymol blue have been added, in a pH range of about 6 to 8.

Kit 200 also includes an acid demand bottle 40 including a primary acid 41 and a base demand bottle 50 including a primary base 51. Primary acid 41 is preferably 0.01% sulfuric acid and primary base 51 is preferably 0.04% sodium hydroxide. Acid 41 and base 51 are specially formulated with sufficient strength to react with a 5 ml sample of water having a pH in the range of about 6 to 8 so that the color of the sample will accurately match the colors of pH chart 20 without undue fading. However, the strength of acid 41 and base 51 should not be too great to be unduly dangerous to handle or to change the pH too quickly so that the acid or base added to the aquarium cannot be added in an accurate manner. Acid demand bottle 40 and base demand bottle 50 are preferably constructed to dispense consistent drops of about 1/27th of a milliliter in volume.

Kit 200 also includes an acid container 70 including a secondary acid 71 and a base container 80 including a secondary base 81. Secondary acid 71 and secondary base 81 are added to aquarium 110 to adjust the pH of water 111 in aquarium 110 to the target value. Acid 71 and base 81 must be chosen carefully so that they are relatively safe to handle, will not cause pH shock, and can be added in appropriately sized amounts, corresponding to drops of primary acid 41 or primary base 51. To accomplish these goals, secondary acid 71 is preferably 30% phosphoric acid in an aqueous solution and secondary base 81 is preferably 100% sodium bicarbonate powder. Kit 200 also includes a spoon 90 of preferably 1/4 teaspoon in size, to dispense consistent quantities of secondary base 81 into aquarium 110.

Aquarium water contains a complex combination of many organic and inorganic components which tend to buffer the pH. Thus, merely knowing the pH and capacity will not necessarily provide sufficient information regarding how much secondary acid or secondary base to add. Rather, more accurate results are achieved by calculating acid demand and base demand in cylinder 100. Furthermore, biological activity in the aquarium tends to lower the pH with time, due to the production of carbon dioxide. Therefore, it is preferable to add a secondary acid or base which will tend to buffer the water in the desired range. Thus, sodium bicarbonate is a preferred secondary base, because it can reduce the pH lowering effects of continued carbon dioxide production in the aquarium system. It is also preferable to re-test the pH of the aquarium two hours after the addition of the secondary acid or base to insure that the pH of the system has stabilized at the appropriate level.

pH test kit 200 also includes conversion chart 60, shown in FIG. 3 for converting the number of drops of primary acid 41 or primary base 51 added to cylinder 100 to adjust the pH of the test sample of water 111, into a quantity of secondary acid 71 or secondary base 81 to be added to aquarium 110 to adjust the pH of water 111 to the desired target value. Chart 60 should be prepared to instruct the hobbyist to add a slight excess of secondary base to create a buffered solution and resist the natural tendency of an aquarium to become undesireably acidic with the passage of time.

To adjust the pH of water 111, in accordance with a preferred embodiment of the invention, a 5 ml sample of water 111 is added to cylinder 100. Two drops (for example) of an indicator such as bromothymol blue are added to the five milliliter sample and the color of the test sample is compared to pH color comparison chart 20 to determine the pH of water 111. If the fish in aquarium 110 require a pH of 6.2 and the water in aquarium 110 has a pH of 7.4 (for example), water 111 has an acid demand and the pH of water 111 in aquarium 110 must be lowered.

To lower the pH of water 111 of aquarium 110, drops of primary acid 41 from acid bottle 40 are added to the test sample in graduated cylinder 100 until the color of the sample in graduated cylinder 100 matches that of the appropriate pH in color chart 20 (e.g. 6.2). By counting the number of drops of primary acid 41 from bottle 40 added into cylinder 100, an acid demand level of water 111 can be determined.

Once the acid demand level of water 111 is known (drops of primary acid 41), the amount of secondary acid 71 needed to adjust water 111 to the desired pH can be determined by use of conversion chart 60, which is prepared based on the known strengths of acids 41 and 71, bases 51 and 81, the volume of the test sample, and the size of the drops from bottles 40 and 50. If, for example, it takes 3 drops of primary acid 41 to lower the pH of the test sample to the desired level, conversion chart 60 indicates that three ml of secondary acid 71 are needed to raise the pH of aquarium 110, for every 10 gallons of water 111 in aquarium 110. If aquarium 110 holds 55 gallons of water 111, conversion chart 60 indicates that 17 ml of secondary acid 71 are needed to lower the pH of water 111 to the target level.

If the pH of the sample of water 111 is lower than the desired pH, it is necessary to raise the pH of water 111 to the target level. To accomplish this, a primary base 51 from base demand bottle 50 is added drop wise to graduated cylinder 100 until the desired color is achieved. Thereafter, in the same manner indicated above, the number of drops of base added to cylinder 100 is converted to an amount of secondary base to be added to aquarium 110. If 2 drops of base 51 were added to the test sample, chart 60 converts this to 8 quarter teaspoon size scoops of sodium bicarbonate.

Conversion chart 60 is prepared, based on a selected volume of test sample, a selected strength of primary acid 41, primary base 51, secondary acid 71 and secondary base 81. Conversion chart 60 corresponds to a 5 milliliter sample, acid 41 being 0.01% sulfuric acid, base 51 being 0.04% sodium hydroxide, acid 71 being 30% aqueous phosphoric acid, base 81 being 100% sodium bicarbonate and spoon 90 holding ¼th of a teaspoon. Substitute conversion charts can be prepared if any of these variables are altered.

When the acid and base components of kit 200 are selected and formulated as set forth above, the pH of aquarium 110 can be adjusted in a convenient manner. For every 10 gallons of water 111 in aquarium 110, approximately 1 ml of secondary acid 71 is added to aquarium 110 for every drop of primary acid added to cylinder 100. For every 10 gallons of water 111 in aquarium 10, approximately two ¼ teaspoon scoops of secondary base 81 are needed per drop of primary base 51 added to cylinder 100. Thus these formulations provide a convenient and safe procedure for accurately adjusting the pH of an aquarium.

It will thus be seen that the objects set forth above, among those made apparent from the preceding description, are efficiently attained and, since certain changes may be made in carrying out the above method in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A kit for adjusting the pH of water in an aquarium, comprising:

container means for receiving a sample of aquarium water of a predetermined volume;

indicator means for adding to the sample of water and coloring the sample to a color corresponding to the pH of the sample;

acid demand container means containing a primary acid, for dispensing the primary acid drop-wise into the container means;

base demand container means including a primary base for dispensing the primary base drop-wise into the container means;

color chart means for determining the pH of a sample by comparing it to a colored portion of the color chart means;

conversion chart means for converting the number of drops of acid or base dispensed into the container means to change the pH of the water sample to a desired level into an amount of a secondary acid or a secondary base to be added to water in an aquarium to change the pH of the water in the aquarium to the desired level;

acid container means containing a secondary acid for lowering the pH of water in an aquarium; and base container means including a secondary base for raising the pH of water in an aquarium.

2. The kit of claim 1, wherein the container is marked and sized for receiving a 5 ml sample of water.

3. The kit of claim 1, wherein the indicator means includes bromothymol blue.

4. The kit of claim 1, wherein the primary acid is 0.01% sulfuric acid.

5. The kit of claim 4, wherein the primary base is 0.04% sodium hydroxide and the acid demand container means and base demand container means are constructed to dispense drops having a volume of about 1/27 ml.

6. The kit of claim 1, wherein the acid demand container means and base demand container means dispense drops having a volume of about 1/27 ml.

7. The kit of claim 1, wherein the primary base is 0.04% sodium hydroxide.

8. The kit of claim 1, wherein the secondary acid is 30% aqueous phosphoric acid.

9. The kit of claim 1, wherein the secondary base is 100% sodium bicarbonate powder.

10. The kit of claim 1, wherein the indicator is bromothymol blue, the primary acid is 0.01% sulfuric acid and the primary base is 0.04% sodium hydroxide.

11. The kit of claim 1, wherein the indicator is bromothymol blue, the primary acid is 0.01% sulfuric acid, the primary base is 0.04% sodium hydroxide, the secondary acid is 30% aqueous phosphoric acid and the secondary base is 100% sodium bicarbonate powder.

12. The kit of claim 11, wherein the conversion chart is constructed and arranged to indicate the addition of approximately 1 ml of 30% phosphoric acid for every ten gallons of water in the aquarium to be adjusted, per drop of primary acid added to the container means.

13. A kit for adjusting the pH of water in an aquarium to a desired pH, comprising:

a container of selected volume;

an indicator which displays easily perceived color changes across the pH range of 6–8;

a first container of primary acid and a second container of secondary acid a first container of primary base and a second container of secondary base;

a color chart for determining the pH of a sample of water from the aquarium by comparing the color of the sample combined with a selected quantity of the indicator to a colored portion of the color chart;

conversion means for converting the amount of primary acid or base from one of said first containers needed to change the pH of a sample of aquarium water of the selected volume to a desired pH to the amount of secondary acid or base from one of said second container needed to be added to the aquarium to change the pH of water in the aquarium to the desired pH.

14. The kit of claim 13, wherein the indicator is bromothymol blue.

15. The kit of claim 13, wherein the conversion means is constructed and arranged to indicate the addition of approximately 1 ml of 30% phosphoric acid for every 10 gallons of water in the aquarium, per drop of acid added to the sample.

* * * * *